United States Patent [19]

O'Rourke

[11] 4,304,023
[45] Dec. 8, 1981

[54] POWER DRIVEN ROTARY TOOTHBRUSH

[76] Inventor: James L. O'Rourke, 6351 Memorial, Detroit, Mich. 48228

[21] Appl. No.: 110,389

[22] Filed: Jan. 8, 1980

Related U.S. Application Data

[63] Continuation-in-part of Ser. No. 898,645, Apr. 21, 1978, Pat. No. 4,181,997.

[51] Int. Cl.$^3$ .............................................. A46B 13/02
[52] U.S. Cl. .................................... 15/23; 15/DIG. 5
[58] Field of Search .......... 15/23, 24, 167 R, DIG. 5, 15/DIG. 6

[56] References Cited

U.S. PATENT DOCUMENTS

| | | | |
|---|---|---|---|
| 1,860,894 | 5/1932 | Lieux | 15/23 |
| 2,840,837 | 7/1958 | Gustems | 15/23 |
| 3,015,833 | 1/1962 | Gilet | 15/23 |
| 3,103,679 | 9/1963 | Clemens | 15/167 R |

FOREIGN PATENT DOCUMENTS

| | | | |
|---|---|---|---|
| 110160 | 4/1900 | Fed. Rep. of Germany | 15/23 |
| 1129650 | 9/1956 | France | 15/23 |

*Primary Examiner*—Edward L. Roberts
*Attorney, Agent, or Firm*—Whittemore, Hulbert & Belknap

[57] ABSTRACT

A tooth-brushing device comprising a brushing unit having a pair of counter-rotating shafts, with bristles projecting radially outwardly from each shaft. The bristles are arranged in a series of clusters spaced from one another along the length of each shaft. Preferably, the clusters of bristles are spaced apart a distance approximately the width of a tooth.

1 Claim, 3 Drawing Figures

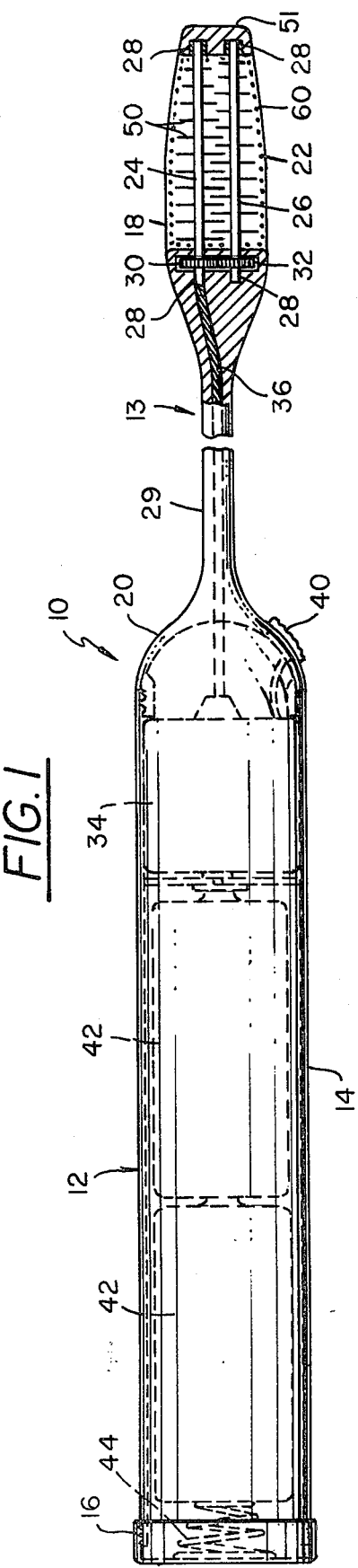
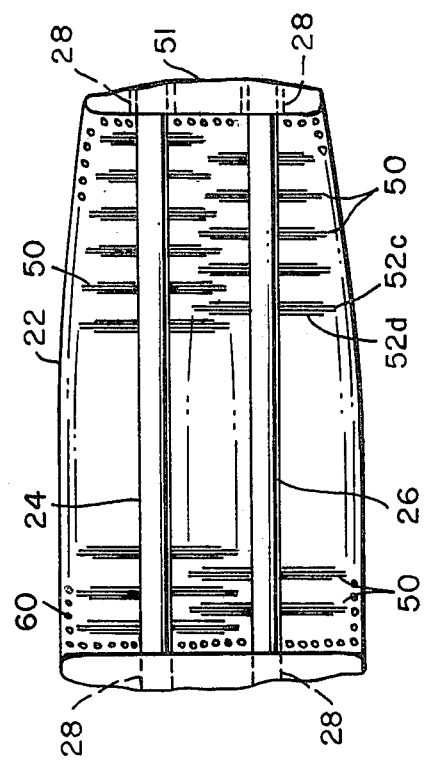
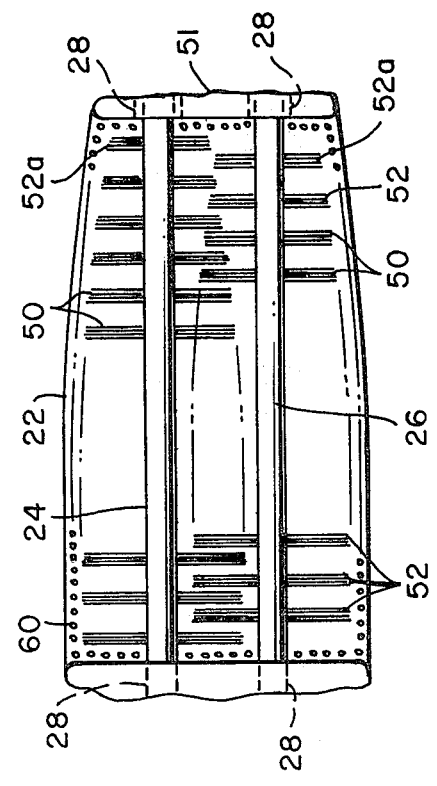

POWER DRIVEN ROTARY TOOTHBRUSH

REFERENCE TO RELATED APPLICATION

This application is a continuation-in-part of my prior application Ser. No. 898,645 filed Apr. 21, 1978, now U.S. Pat. No. 4,181,997.

This invention relates generally to toothbrushes and refers more particularly to a toothbrush having bristles projecting from a pair of power driven shafts.

BACKGROUND AND SUMMARY OF THE INVENTION

Toothbrushes of the rotary, power driven type, of which I am aware, have the bristles uniformly distributed along the length of each shaft. An example of one such toothbrush is shown in U.S. Pat. No. 2,285,865. One of the problems with toothbrushes of this type is that they do not brush satisfactorily between the teeth.

I have discovered that by arranging the bristles in clusters along the length of each shaft, and preferably by spacing the clusters apart a distance approximating the width of a tooth, much more effective brushing between the teeth, where most cavities originate, can be achieved.

These and other objects of the invention will become apparent as the following description proceeds, especially when considered with the accompanying drawings.

BRIEF DESCRIPTION OF THE DRAWINGS

FIG. 1 is an elevational view, with parts in section, of a toothbrush constructed in accordance with my invention.

FIG. 2 is an enlarged fragmentary view of a portion of FIG. 1.

FIG. 3 is similar to FIG. 2 but shows a modification.

DETAILED DESCRIPTION

Referring now more particularly to the drawings and especially FIGS. 1 and 2 thereof, the toothbrush 10 comprises a body 12 and a brushing unit 13.

The body 12 comprises an elongated open-ended cylindrical tube 14 having a cap 16 threaded on and closing one end. The brushing unit has a head 18 at one end and a cap portion 20 at the opposite end threaded onto the end of the tube 14 opposite cap 16.

The head 18 of the brushing unit has an elongated rear wall 22, along the front side of which extends a pair of shafts 24 and 26. These shafts 24 and 26 are rotatably supported in laterally spaced, parallel relation to each other by journals 28 at opposite ends of the rear wall 22. Gears 30 and 32 secured to the respective shafts mesh with one another so as to constrain the shafts to rotate in opposite directions.

Rotation of the shafts is accomplished by means of an electric motor 34 in the body 12 of the toothbrush which when operated drives a flexible shaft 36 extending through a passage in the cap portion 20 and midportion 29 and connected to the shaft 24. The direction of motor rotation is such as to cause the shafts to rotate in directions to brush the teeth away from the gums. There is an on-off switch 40 mounted externally on the cap portion 20 of the brushing unit in a position for convenient manual operation to turn the electric motor on or off, as desired. The motor 34 is energized by any suitable means, in this instance by dry-cell batteries 42 contained within the body 12 and held in electrical contact with one another and with the motor by a coil spring 44 compressed by the cap 16 against one end of one of the batteries.

A series of flexible bristles 50 project radially outwardly from each of the shafts 24 and 26. The bristles 50 are arranged in a series of clusters or groups 52 spaced from one another along the length of each shaft. There are a plurality of bristles in each cluster distributed in a circular array about the shaft axis and projecting radially outwardly therefrom. The bristles do not contact the rear wall 22 when they rotate. The clusters on each shaft are spaced apart a distance which may vary but preferably, as shown, approximates the width of a single human tooth. The clusters of bristles on each shaft are staggered with respect to the clusters of bristles on the other shaft. The shafts are spaced close enough together so that the clusters of bristles on each shaft extend into the spaces between the clusters of bristles on the other shaft. A compact structure is thus provided which fits easily into the mouth. However, the shaft spacing and bristle length is such that the bristles on one shaft do not touch the other shaft.

The bristles near the end 51 of the head 18 of the toothbrush are progressively shorter in a direction toward that end, producing a taper as clearly shown in the drawings. The purpose of this is to enable more convenient brushing of the back teeth. Thus in FIG. 2 the clusters of bristles 52a on both shafts at the end 51 of the head of the toothbrush are noticeably shorter than those at the opposite end, to an extent that the bristles in each cluster 52a do not quite extend into the adjacent space between the clusters of bristles on the other shaft, although the staggered relation of the clusters of bristles on the two shafts exists throughout the full length of both shafts.

FIG. 2 shows a construction in which all of the bristles in each cluster are of the same length throughout a full 360° around the shaft. These bristles are preferably of uniform flexibility and will brush the teeth and will also get in between the teeth with a sweeping action. Brushing between the teeth, where most cavities originate, is very important. The spacing and distribution of the bristles into clusters enables more effective brushing between the teeth.

FIG. 3 shows a modification in which some of the bristles 52c in each cluster are longer than others 52d. The longer bristles are believed to be more effective in brushing between the teeth and the shorter bristles are believed to be more effective in brushing the surfaces of the teeth. Preferably the longer bristles are more flexible than the shorter bristles.

A line of bristles 60 extend outwardly from the rear wall 22 of the head completely around the clusters of bristles on both shafts to reduce spray produced by the rotation of the shafts. The bristles 60 extend at right angles to a plane containing the longitudinal axes of the two shafts.

I claim:

1. A tooth-brushing device comprising a brushing unit having a pair of shafts, means rotatably supporting said shafts in laterally spaced, parallel relation to each other, flexible bristles projecting radially outwardly from each shaft, said bristles being arranged in a series of clusters spaced from one another along the length of each shaft, there being a plurality of bristles in each cluster distributed in a circular array about the shaft axis and projecting radially outwardly therefrom, and means for counter-rotating said shafts in directions to brush the teeth away from the gums, said clusters on each shaft being spaced apart so that the ends of the bristles in each cluster are separated from the ends of the bristles in adjacent clusters by a distance approximating the width of a tooth, some of the bristles in each cluster being longer and more flexible than others in the same cluster, the longer more flexible bristles being more effective to brush between the teeth.

* * * * *